United States Patent [19]

Carlton et al.

[11] Patent Number: 5,409,707

[45] Date of Patent: Apr. 25, 1995

[54] OIL EMULSIFYING EXTENDER FORMULATION IMPARTING SUSTAINING PROPERTIES TO AGRICULTURAL PRODUCTS

[75] Inventors: W. Reid Carlton, Longwood, Fla.; Thomas P. Lahey, Newport Beach, Calif.

[73] Assignee: Carlton Lahey Chemicals, Inc., Longwood, Fla.

[21] Appl. No.: 92,542

[22] Filed: Jul. 16, 1993

Related U.S. Application Data

[63] Continuation of Ser. No. 711,929, Jun. 7, 1991, abandoned, which is a continuation-in-part of Ser. No. 565,023, Aug. 8, 1990, abandoned.

[51] Int. Cl.⁶ .............................. A01N 25/30
[52] U.S. Cl. .................................. 424/405
[58] Field of Search .............. 424/78.1, 405

[56] References Cited

U.S. PATENT DOCUMENTS

| | | | |
|---|---|---|---|
| Re. 33,670 | 8/1991 | Maglio | 424/408 |
| 3,930,010 | 12/1975 | Klopping . | |
| 3,948,636 | 4/1976 | Marks . | |
| 3,984,570 | 10/1976 | Bent et al. . | |
| 4,110,431 | 8/1978 | Oita | 424/364 |
| 4,212,870 | 7/1980 | Gibbs . | |
| 4,594,184 | 6/1986 | Cook et al. . | |
| 4,657,582 | 4/1987 | Huber | 71/121 |
| 4,747,977 | 5/1988 | Whitehead et al. . | |
| 4,902,333 | 2/1990 | Quimby, Jr. . | |
| 4,933,167 | 6/1990 | Scher et al. | 514/140 |
| 4,992,194 | 2/1991 | Liberati et al. . | |

FOREIGN PATENT DOCUMENTS

| | | |
|---|---|---|
| 243872 | 4/1987 | European Pat. Off. . |
| 1604859 | 12/1981 | United Kingdom . |

OTHER PUBLICATIONS

Chem. Abstract 99:153891k Mikasa.
Chem. Abstract 94:78426d Shell.

*Primary Examiner*—Thurman K. Page
*Assistant Examiner*—Peter F. Kulkosky
*Attorney, Agent, or Firm*—Burns, Doane, Swecker & Mathis

[57] ABSTRACT

An extender composition for use with agricultural economic poisons includes two or more nonionic surfactants having H/L (hydrophilic/lipophilic) balance values of 10 to 15, oxyhydrocarbon solvent, and an inorganic polyoxide such as a polyphosphate or its salt and optionally a strong inorganic base. This composition extends the effective life of these agricultural products and reduces the amount of such products needed to achieve desired effects.

21 Claims, No Drawings

OIL EMULSIFYING EXTENDER FORMULATION IMPARTING SUSTAINING PROPERTIES TO AGRICULTURAL PRODUCTS

Cross-Reference to Related Application

This application is a continuation of application Ser. No. 711,929, filed Jun. 7, 1991,now abandoned, which is a continuation-in-part of U.S. patent application Ser. No. 565,023, filed Aug. 8, 1990, incorporated herein by reference and now abandoned.

TECHNICAL FIELD

Compositions are provided for use as agricultural emulsifying extenders with sustaining properties imparted to the agricultural products.

Background of the Invention

There is a critical need to minimize the quantity and frequency of application of pesticides and other agricultural products to crops and to increase the effectiveness of pest control using existing pesticides. There are many instances where increasing amounts of newly developed and increasingly toxic economic poisons are required to kill or control pests on plants and crops. Increasing public awareness of residual surface and systemic pesticide concentrations in fruit and vegetables has resulted in chemical testing of fruits and vegetables for the pesticides with high concentrations in crops resulting in increased consumer cost and crop devaluation. Additionally, bacteria and insects which are not targeted pests but are beneficial to the crops are often destroyed as a result of the application of presently formulated economic poisons at manufacturer's labeled rates. The 5 to 30 day period of pest control following application of some economic poisons typically requires a 90 to 180 day period before recommended subsequent reapplication. This required reapplication interval allows for significant repopulation of the targeted pest(s) in a given growing season or requires an additional application of other economic poisons at both significant environmental and economic cost to the grower.

Recognizing the labeled restrictions on application of economic poisons, the farmer has resorted to reducing the recommended concentration of economic poisons using extenders and increased the frequency of spray application. By decreasing the quantity of sprayed pesticide per acre crop, the residual pesticide concentration on the crops is minimized. However, the acquired resistance by the targeted pests to the economic poisons is increased by this practice. Additionally, the higher frequency of sprayed application is costly, and the duration of pest control on the crop is decreased. One of the problems is loss of the applied economic poison from the targeted surfaces by the effects of rainfall or condensate dripping off of those plant surfaces.

There is, therefore, a substantial interest in being able to significantly improve the duration of pest control and activity of the applied economic poison formulations to minimize the concentration of pesticides on the fruit or vegetables, and the acquired resistance by the targeted pests to the economic poisons.

DESCRIPTION OF THE RELEVANT LITERATURE

U.S. Pat. No. 3,930,010 describes a fungicide which, when formulated with nonionic and anionic surfactants at or above their critical micelle concentration in the sprayed composition, yields improved fungicidal activity with continuing safety to the treated plants. U.S. Pat. No. 3,984,570 to Bent et al. describes certain surface active agents which are used to combat specific fungal diseases in plants. U.S. Pat. No. 4,212,870 to Gibbs discloses an insecticide with systemic activity which is applied with the aid of surfactants which are essential to the insecticidal activity. U.S. Pat. No. 3,948,636 to Marks shows pesticide compositions which include 10–60% active ingredient, 1–10% surfactant and 0.02 to 1% of a heteropolysaccharide gum (all by weight). U.S. Pat. No. 4,902,333 to Quimby Jr. shows a spray formulation for use in conjunction with fungal pathogens which enables the water to remain in moisturizing contact with the fungus. This formulation includes a water-in-oil emulsion including wax or lecithin plus calcium salt. British Patent No. 1,604,859 discloses the use of nonionic and cationic surfactant in conjunction with monohydric alcohols as insecticidal formulations with low host (human) toxicity and high insecticidal mortality. European Patent Application No. 243,872 of Kimisk Vaerk Koze A.S. shows pesticidal concentrates which include an oily suspension phase carrying a surfactant which includes a $C_6$–$C_{30}$ chain-containing moiety. These patents are not intended to be exhaustive, but merely illustrative of the various uses of surfactant(s) essential to the effective application, adsorption, and activity of fungicidal and insecticidal products, which disclosures are incorporated herein by reference.

SUMMARY OF THE INVENTION

We have now discovered an extender composition for use with economic poisons (agricultural pesticides) which imparts sustained activity to economic poisons and substantially reduces the quantity or concentration of these materials required to effect pest control or eradication. This composition can be classed broadly as an oil emulsifying composition.

Viewed generally, the extender composition comprises two or more nonionic surfactants; more particularly, two or more nonionic surfactants each having H/L balances in the range of 11 to 15; water-immiscible organic liquid solvent; inorganic polyoxide or salt thereof; and, optionally, inorganic base. The composition can be formulated into an aqueous solution containing a mixture of nonionic surfactants, organic solvent, inorganic polyoxide or salt thereof and, optionally, inorganic hydroxide. When the extender compositions disclosed herein are combined with commercially formulated economic poisons which are in the form of dry flowable powders or emulsifiable concentrates, optionally diluted with water, and applied to row crops and citrus, substantially improved pest control is achieved with sustained activity of the economic poison at significantly reduced concentrations of the economic poison per acre of treated crop or citrus. In addition, the presence of this extender composition appears to impart unexpected additional activity to economic pesticides including, for example, the ability to prevent fertilization of pest eggs and to eradicate insects, mites, fungus and bacteria at all stages of their development including stages before they have had a chance to produce mutated resistant offspring.

In other aspects, this invention provides economic poison formulations which include the subject extender compositions together with economic poisons, water-diluted sprayable formulations which include the economic poison and the extender, and methods of treating crops by applying these formulations, typically at use levels or frequencies below those used for the economic poison without the present extender composition.

DESCRIPTION OF THE SPECIFIC EMBODIMENTS

Compositions are provided which impart sustained and increased activity to economic poisons at significantly reduced concentrations of the economic poison per acre of treated crop or citrus. The components of the composition will be liquids, granular crystalline solids, and emulsifiable concentrates which are dissolved or emulsified in an aqueous solution. The components include two or more nonionic surfactants, inorganic polyoxide and/or salt thereof, organic solvent and, optionally, a strong inorganic base such as sodium, magnesium, calcium or potassium hydroxide.

The Surfactants

The nonionic surfactants can be selected from alkyl polyether alcohols, alkyl phenoxy polyethers, alkyl phenoxy polyether alcohols, alcohol-terminated ethoxylated linear alcohols, secondary linear or branched chain alcohols condensed with ethylene or propylene oxide, aromatic ethers, poly(oxyethylene)polyesters, poly(oxyethylene) sorbitol esters, and alkyl cycloaliphatic ethers which have H/L balance values between 10 and 15. We have discovered that a mixture of at least two nonionic surfactants having an H/L balance between 10 and 15 gives best results. H/L balance is a measure of hydrophilicity/lipophilicity and is determined by partitioning a material between water and n-octane. Preferably, the two or more nonionic surfactants have H/L balance values between 11 and 14 and particularly between 13 and 13.5.

To constitute a suitable mixture, typically each of the several surfactants shall make up at least about 10% of the total surfactant. Binary mixtures should range from 90:10 to 10:90, preferably 80:20 to 20:80 and especially 75:25 to 25:75 on a weight basis.

In preferred compositions, one component in the nonionic surfactant mixture meeting these values is a secondary alcohol ethoxylate which contains between 5 and 22 carbon atoms in the alcohol portion condensed with between 5 and 15 ethylene oxide units, preferably a secondary alcohol with between 11 and 15 carbon atoms condensed with 9 ethylene oxide units. 4-tetradecyloxy 9 ethoxylate is a preferred first surfactant. A second component in the nonionic surfactant mixture which meets the H/L values is a p-alkyl (alkyl of 6-20 carbons) phenoxy(polyethyleneoxy)ethanol. We have found the preferred structure of this second nonionic surfactant is para octyl or para nonyl phenol condensed with from about 4 to about 20 units of ethylene oxide, especially with about 9 units of ethylene oxide. A third nonionic surfactant is often present. This material is a sorbitol polyester polyethoxylate which is composed of up to 5 fatty acids esterified to the sorbitol hydroxyl groups. The preferred composition is a sorbitol pentaoleate molecule condensed with on average of from 5 to 15 and especially about 9 molecules of ethylene oxide. Other materials such as stearates, laurates and the like can be used. The oleates are preferred. These materials are often present in commercial crop oil and can be added separately.

One can, in addition, use mixtures of secondary alcohol ethoxylates and/or members of the ethoxylated alkylphenols.

The Inorganic Polyoxide

The extender formulation includes inorganic polyoxide or salt thereof. The inorganic polyoxide or salt thereof can be an oxide of phosphorus, silicon or boron, preferably a polyoxide such as metasilicate, pyrophosphate, triborate, more preferably sodium metasilicate, sodium tetraborate, sodium pyroborate, or sodium tripolyphosphate. In other words, the inorganic polyoxide can include, for example, mono-, di- or tri- sodium or potassium phosphate, mono-, di- or tri- sodium or potassium hypophosphate, mono-, di- or tri- sodium or potassium metaphosphate, mono-, di- or tri- sodium or potassium orthophosphate, sodium or potassium pyrophosphate, sodium or potassium tripolyphosphate, sodium or potassium silicate, sodium or potassium disilicate, sodium or potassium metasilicate, sodium or potassium orthosilicate, sodium or potassium metaborate, sodium or potassium tetraborate. We have found that sodium tripolyphosphate is preferred for use in our formulation. Mixtures of polyoxides can be used, if desired.

The Organic Solvent

The organic solvent can be any oxyhydrocarbon liquid (e.g., alcohol, ether, or ketone) which is completely miscible with water, with at least two but not more than ten carbon atoms, preferably two to six carbon atoms. The alcohol may be a diol or triol, with either esterification or etherization of at least one but not all of the hydroxyl groups to include the cellosolves and the acetates and propionates of the polyols. We have found acetone, methyl ethyl ketone, butyl cellosolve (2butoxy ethanol), propylene glycol and butylene glycol to be superior solvents for this formulation, with 2-butoxy ethanol (butyl cellosolve) being the preferred solvent in our composition.

The Hydroxide

Sodium, potassium, calcium, or magnesium hydroxide is an optional component which can be used to adjust the pH of the combined components to a range of 11-14 with sodium hydroxide being preferred in our composition. This hydroxide works together with the polyoxide to buffer the composition in the 11-14 range.

The Overall Extender Composition

The overall extender composition comprises the following proportions of the above-described materials:

| | Weight Proportion |
|---|---|
| 2 or more nonionic surfactants with H/L balance of 11-15 | 1 part |
| organic solvent | 0.1 to 1 |
| inorganic polyoxide | 0.25 to 2 |
| inorganic hydroxide (optional) | 0 to 1 |
| ethoxylated sorbitol ester (optional) | 0 to 1 |

A preferred extender composition comprises the following:

| | Weight Proportion |
|---|---|
| a 5 to 22 carbon atom secondary alcohol 5-15 | 1 part |

|  | Weight Proportion |
| --- | --- |
| ethoxylate plus a paroctyl or paranonyl phenol with 4–12 ethoxylates in a weight ratio of 90:10 to 10:90 | |
| oxyhydrocarbon solvent | 0.1 to 1 |
| inorganic polyoxide salt | 0.25 to 2 |
| sodium or potassium hydroxide | 0 to 1 |
| ethoxylated sorbitan ester | 0 to 1 |

More preferred compositions comprise:

|  | Weight Proportion |
| --- | --- |
| a 12 to 16 carbon atom secondary alcohol 7-12 ethoxylate plus p-aoctyl or anonyl phenol 4-20 ethoxylate in a weight ratio of 80:20 to 20:80 | 1 part |
| a solvent made up of acetone, methyl ethyl ketone, butyl cellosolve, propylene glycol and/or butylene glycol | 0.2 to 0.8 |
| inorganic phosphate or silicate | 0.35 to 1.75 |
| sodium or potassium hydroxide | 0 to 0.75 |
| sorbitan oleate - 5-15 ethoxylate | 0 to 0.75 |

This extender formulation can be put together by simply mixing the various components until homogenous in any suitable mixer.

The extender can contain additional materials such as dyes or other additives without departing from the spirit of the invention.

Formulations with Poisons

The extender, when used, is formulated with one or more economic poisons. Any sprayable poison-including insecticides, fungicides, miticides and the like can be used, without limitation.

Representative art-known poisons are shown in Table 1.

TABLE 1
Partial List of Economic Poisons which can be used in Conjunction with Oil Emulsifying Extender Imparting Sustaining Properties Acaraben
Agrimek
Aliette
Avermectin $B_1$
Azinphos-methyl
Benelate
Carazol
Comite
Cygon 4EG
Citrus Spray Oil FC 435-66
Crop Oil
Cupric ammonium hydroxide
Copper Count-N
Diazinon
Dicofol 4E
Dicofol 4EC
Dicofol 1.6EC
Difolatan
Dimethoate
Ethion
Ethion plus crop oil
Guthion
Lorsban
Malathion
Methidathion
Metasystox-R
Nemacur 3
Nemacur 15G
Propargite
Pyrethins

TABLE 1-continued
Partial List of Economic Poisons which can be used in Conjunction with Oil Emulsifying Extender Imparting Sustaining Properties Supracide
Vendex 50 WP and 4L Crop oil is one of the more preferred materials which has its effectiveness enhanced by the present invention as are mixtures of crop oil plus other economic poisons.

In these formulations with the extender, the amount of poison can range from its normal use concentration and use levels known in the art to concentrations and use levels as low as 1/5 or less than those used conventionally.

The extender is combined with the commercial economic poison(s) emulsifiable concentrate as supplied by the manufacturer. The mixture is then blended until homogeneous (solution or emulsion). The formulation is simultaneously or serially diluted (dissolved or completely emulsified) in water, and is then applied to the crops again at use levels ranging from 20% to 100% of normal levels and at frequencies of application ranging from 20% to 100% of normal.

EXAMPLE 1

In order to demonstrate the subject invention, the following experiment was carried out.

The formulation was prepared as follows: to 200 grams of 4-tetradecyloxy (polyethyleneoxy) ethanol was added 90 grams of 2-butoxy-ethanol with stirring at room temperature. To this mixture was then added 360 grams of a 25% w/w solution of sodium tripolyphosphate in water. This mixture was again stirred at room temperature until thoroughly mixed. To this mixture was then added 90 grams of p-octylphenoxy (polyethyleneoxy) ethanol, 10 grams of sodium hydroxide pellets, and the mixture was stirred until all the sodium hydroxide was dissolved. To this mixture was added 120 grams (2 fluid ounces) of Agrimek (Avermectin $B_1$) pesticide which is used to control citrus rust mites and other pests on citrus. To this mixture was added 1 gallon of Citrus Spray Oil FC 435-66 (crop oil) and 150 grams of poly-(oxyethylene) sorbitol pentaoleate and stirred until uniformly mixed. The combined components of the formulation were then diluted into 5 gallons of water and mixed until emulsified and transferred into a spray tank on a helicopter.

To test the effect of the formulation, the emulsified economic poison formulation described above was spray applied at the above concentrations per one acre of Florida navel oranges, which were heavily infested with citrus rust mites. The results of the experiment indicated that total targeted pest control was obtained for 120 days following application of the emulsified pesticide.

A control experiment to validate the efficacy of the invention was also performed using a mixture of 54 grams of Agrimek (Avermectin $B_1$) in 1 gallon of Citrus Spray Oil FC 435-66 (crop oil) emulsified in 5 gallons of water. This mixture was applied at these concentrations per one acre of the same crop of Florida navel oranges with identical infestation by citrus rust mites. No targeted pest control was observed using this protocol for application of the agricultural product.

Additionally, in a third experiment using the manufacturer's recommended application protocol, 370 grams of Agrimek (Avermectin B₁) was dissolved in 1 gallon of Citrus Spray Oil FC-435-66 (crop oil) and was emulsified in 99 gallons of water and spray applied at these concentrations to one acre the same crop of Florida navel oranges with identical infestation by citrus rust mites. This resulted in targeted pest control for 65 days.

Thus, the experiment showed that for over 120 days, the crops treated with a significantly lesser quantity of pesticide applied with the emulsifying and extending formula exhibited total pest control. The crops that were not treated with the formulation but with an identical quantity of pesticide in crop oil were not controlled whatsoever. Using significantly higher quantities of the Agrimek (Avermectin B₁) per the manufacturer's recommended application protocol, pest control was observed for only 65 days. The results of this experiment are presented in Table 2.

TABLE 2

Efficacy of Emulsifying Extender Imparting Sustaining Properties on Citrus Rust Mites

| Composition of Economic Poison | Pest Control Period, days |
|---|---|
| 1 gal. crop oil | 0 |
| 5 gal. water | |
| 120 grams Agrimek (Avermectin $B_1$) | |
| 1 gal. crop oil | 65 |
| 99 gallons water | |
| 370 grams Agrimek (Avermectin $B_1$) | |
| 1 gal. crop oil | 120+ |
| 5 gal. water | |
| 54 grams Agrimek (Avermectin $B_1$) | |
| 150 gr. poly(oxyethylene) sorbitol pentaoleate | |
| 200 gr. 4-tetradecyloxy (polyethoxy) ethanol | |
| 320 gr. 25% sodium tripolyphosphate | |
| 90 gr. 2-butoxy ethanol | |
| 90 gr. p-octylphenoxy poly(ethyleneoxy) ethanol | |
| 10 gr. sodium hydroxide | |

EXAMPLE 2

Similar experiments were performed on one acre and ten acre plots of Florida navel oranges using the same emulsifying extender formula but with ethion instead of Avermectin $B_1$. Our experiment using the ethion mixed with the emulsifying extender composition resulted in extended pest control (over 150 days) at less than 40% of the manufacturer's recommended application protocol. Usage of the ethion without the oil emulsifying extender imparting sustaining properties at recommended application protocol provided significantly lesser pest control for a period of 30 days requiring additional reapplication of other economic poisons to control the targeted pests.

EXAMPLE 3

A stock solution of the extender formulation of the invention was prepared including the following materials in the following proportions:

200 g. 4-tetradecyl alcohol 9-ethoxylate
90 g. p-octylphenol 9-ethoxylate
90 g. 2-butoxy-ethanol
90 g. sodium triphosphate
10 g. sodium hydroxide
270 g. water This material was mixed with spray oil and water and sprayed on citrus at the following rates:

0.5 and 1 gallon/acre extender
0.75 and 1.5 gallon/acre spray oil
124.75 and 123.5 gallon/acre water For comparison Vendex was applied at typical conventional use levels to adjacent trees. An equal number of leaves were examined in each of the three test groves.

The composition of the invention at 1.0 gallons/acre showed 9 leaves with rust mites-6 with 1 mite, 1 with 2 mites, 1 with 9 mites and 1 with 18 mites. The composition at half rate showed 18 leaves with mites-16 with 1 mite, 1 with 2 mites, and 1 with 5 mites. In contrast, the prior art material showed 19 leaves with mites-10 with 2 or more in one test and 39 leaves with mites-31 with 2 or more in a replication.

EXAMPLE 4

A test of product longevity was carried out using the extender composition of Example 3.

In a first test, 64 oz.—extender
128 oz.—crop oil 435
54 oz.—Citri-Film
1280 oz.—water was applied per acre to navel orange trees. Rust mite counts were carried out prior to spraying and 64 and 96 days thereafter.

Rust mite counts of 6–75 were observed initially. After the elapsed time (64 or 96 days), no more than 2 mites were observed.

EXAMPLE 5

Example 4 was repeated using Marcotts tangerine trees as the test crop.

The spray was 70.0 oz. extender, 128 oz. crop oil, 640 oz. water per acre.

Rust mite counts went from 10–28 before spraying, to from 0–3 33 and 67 days thereafter.

EXAMPLE 6

The test of Example 4 was repeated using valencia orange trees as the test crop. The spray was 76.0 oz. extender, 384 oz. 435 crop oil, 1920 oz. water per acre. Rust mite populations were reduced a factor of at least 10 and repeated at these low levels for 55 days.

EXAMPLE 7

One gallon of the extender of Example 3 was mixed with 1.5 oz. of Carazol and applied to an acre of citrus with 250 gallons of water.

The same formulation without extender was applied for comparison. The test material reduced rust mite counts from 45–47 to 1–3. The comparison formulation only reduced mite counts from 45–47 to 44–45.

EXAMPLE 8

The experiment of Example 7 is repeated using Durstan-0.00125% as an anti-aphid agent. When extender is present, all aphids are killed. When not present, about 50% are killed.

It is evident from the above results that greatly improved performance is achieved using the emulsifying extender for use with economic poisons to control pests over extended periods of time at reduced usage rates. In this manner, a single application of the economic poison using the emulsifying extender is sufficient for pest control during an entire growing season of crop(s). In addition, the use of the emulsifying extender in conjunction with the economic poisons increases efficiency, crop yield, reduces the quantity of pesticides applied and the residual pesticide on the crop, and provides for a variety of economies.

Although the foregoing invention has been described in some detail by way of illustration, and examples for purposes of clarity and understanding, it will be obvious that certain changes may be practiced within the scope of the appended claims.

We claim:

1. An agricultural emulsifying extender composition for liquid spray-applied pesticide, said agricultural emulsifying extender composition imparting sustaining properties when combined with said pesticide, the extender composition comprisin, g:
   - 1 part by weight of a mixture of two or more nonionic surfactant each having an L/H balance of 11 to 15, said mixture consisting essentially of a secondary alcohol ethoxylate having 5 to 22 carbon atoms in its alcohol portion and 5 to 15 ethylene oxide units in its ethoxylate portion and a p-alkyl phenoxy (polyethyleneoxy) ethanol having 6 to 20 carbon atoms in its alkyl portion,
   - 0.25 to 2 parts of inorganic polyoxide or salt thereof and
   - 0.1 to 1 part of water-miscible oxyhydrocarbon organic solvent.

2. The agricultural emulsifying extender composition imparting sustaining properties according to claim 1, wherein said mixture of two or more nonionic surfactants includes at least about 10% of alkyl phenoxy (polyethyleneoxy) ethanol.

3. The agricultural emulsifying extender composition imparting sustaining properties according to claim 1, wherein said mixture of two or more nonionic surfactants includes at least about 10% of p-octyl phenoxy (polyethyleneoxy) ethanol.

4. The agricultural emulsifying extender composition imparting sustaining properties according to claim 1, wherein said a mixture of nonionic surfactants includes at least about 10% of p-nonyl phenoxy (polyethyleneoxy) ethanol.

5. The agricultural emulsifying extender composition imparting sustaining properties according to claim 1, wherein said mixture of nonionic surfactants include at least about 10% of an alkyl phenolate condensed with about 9 units of ethylene oxide.

6. The agricultural emulsifying extender composition imparting sustaining properties according to claim 1, wherein said inorganic polyoxide or salt thereof is a polyoxide of phosphorus.

7. The agricultural emulsifying extender composition imparting sustaining properties according to claim 1, wherein said inorganic polyoxide or salt thereof is a polyoxide of silica.

8. The agricultural emulsifying extender composition imparting sustaining properties according to claim 1, wherein said inorganic polyoxide or salt thereof is sodium metasilicate.

9. The agricultural emulsifying extender composition Imparting sustaining properties according to claim 1, herein said inorganic polyoxide or salt thereof is sodium tripolyphosphate.

10. The agricultural emulsifying extender composition imparting sustaining properties according to claim 1, wherein said inorganic polyoxide or salt thereof is a salt of boron.

11. The agricultural emulsifying extender composition imparting sustaining properties according to claim 10, wherein said inorganic polyoxide or salt thereof is sodium pyroborate.

12. The agricultural emulsifying extender composition imparting sustaining properties according to claim 10, wherein said inorganic polyoxide or salt thereof is sodium tetraborate.

13. The agricultural emulsifying extender composition imparting sustaining properties according to claim 1, additionally comprising sodium or potassium hydroxide added to the formulation to adjust the pH of the solution to between 7 and 14.

14. The agricultural emulsifying extender composition imparting sustaining properties according to claim 1, (wherein said organic solvent is 2-butoxyethanol.

15. The agricultural emulsifying extender composition imparting sustaining properties according to claim 1, wherein said organic solvent is propylene glycol.

16. The agricultural emulsifying extender composition imparting sustaining properties according to claim 1, wherein said organic solvent is butylene glycol.

17. An agricultural pesticide formulation comprising pesticide in combination with the extender composition of claim 1.

18. The formulation of claim 17 additionally comprising water diluent to a sprayable concentration of pesticide.

19. The formulation of claim 17 wherein the pesticide comprises crop oil.

20. The formulation of claim 19 wherein the extender includes poly(ethyleneoxy) sorbitol oleate ester as a nonionic surfactant.

21. The method for controlling pests on crops comprising spray applying the formulation of claim 18 to crops said extender imparting sustaining properties to the pesticide and increasing the efficacy of the pesticide.

* * * * *